United States Patent [19]

Jones

[11] 3,937,091
[45] Feb. 10, 1976

[54] APPARATUS FOR SAMPLING A LIQUID
[76] Inventor: Richard W. Jones, 56 Trent Lane, Kings Newton, Derbyshire, England
[22] Filed: July 26, 1972
[21] Appl. No.: 275,403

[52] U.S. Cl.............................................. 73/425.4 R
[51] Int. Cl.².......................................... G01N 01/14
[58] Field of Search........ 73/425.4 R, 422 R, 421 R

[56] References Cited
UNITED STATES PATENTS

| | | | |
|---|---|---|---|
| 2,841,012 | 7/1958 | Romer | 73/421 R |
| 2,934,959 | 3/1960 | Johnson | 73/422 R |
| 3,247,721 | 4/1966 | Johnson | 73/425.4 R |
| 3,377,868 | 4/1968 | Dowling et al. | 73/425.4 R |

Primary Examiner—Donald O. Woodiel
Assistant Examiner—Daniel M. Yasich
Attorney, Agent, or Firm—Henderson & Strom

[57] ABSTRACT

An apparatus for sampling a liquid includes a container for immersible in the liquid with a capillary tube liquid inlet. Gas outlet means communicating with the container, the gas outlet means defining an orifice restricting outflow of gas from the container, and the gas outlet means also defining a gas release port for location, in use, below the surface of the liquid, and adjusting means for adjusting the vertical position of the gas release port with respect to the liquid inlet so as to regulate the rate of flow of gas from the container.

1 Claim, 3 Drawing Figures 3,937,091

APPARATUS FOR SAMPLING A LIQUID

BACKGROUND OF THE INVENTION

This invention relates to apparatus for sampling a liquid over an extended period.

Many known sampling devices incorporate pumps and motors, the speed or the frequency of operation of the pump being controlled by auxiliary devices. Other known sampling devices incorporate a number of evacuated bottles into which, when a valve in the neck of each bottle is opened, a small quantity of the liquid is sucked. The valves are usually controlled by a timing device. Some sampling devices are operated by compressed air. The sampling device is located beneath the surface of the liquid and liquid enters a chamber within the device through a non-return valve. At intervals determined by an auxillary device, a pulse of compressed air purges the chamber and forces the liquid through a tube to a collecting bottle above the surface of the liquid. All these devices are of elaborate construction and require careful maintenance. They are usually bulky and cannot be left unattended at remote locations; for example on a river bank. The pump and compressed air types also require a power supply.

A need exists for a liquid sampling apparatus which is of particularly simple construction.

SUMMARY OF THE INVENTION

According to the present invention there is provided a method of sampling a liquid comprising immersing a container in the liquid, permitting liquid to enter the container through an inlet therein, and controlling the rate of flow of liquid into the container by regulating flow of gas from an outlet of the container.

The invention also resides in apparatus for sampling a liquid, comprising a container for immersion in the liquid, a liquid inlet to the container, gas outlet means communicating with the container, the gas outlet means defining an orifice restricting outflow of gas from the container, and the gas outlet means also defining a gas release port for location, in use, below the surface of the liquid, and adjusting means for adjusting the vertical position of the gas release port with respect to the liquid inlet so as to regulate the rate of flow of gas from the container.

The invention further resides in apparatus for sampling a liquid comprising a container for immersion in the liquid, a liquid inlet to the container, gas outlet means communicating with the container, the gas outlet means defining an orifice restricting the outflow of gas from the container and the gas outlet means also defining a gas release port for location, in use, above the surface of the liquid.

It is an object of this invention to provide a liquid sampling apparatus which is effective, reliable, and of simple construction.

DESCRIPTION OF THE PREFERRED EMBODIMENTS

Figure 1:
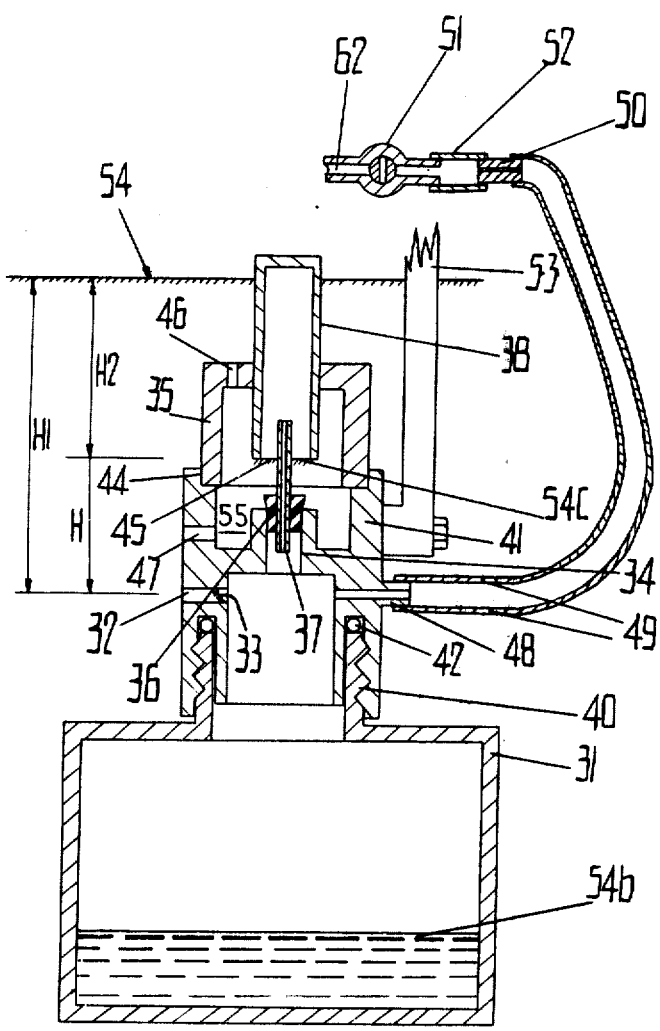
FIG. 1 is a sectional view of a first embodiment of the invention.

FIG. 1 shows an apparatus constructed in accordance with this invention and incorporating a single capillary tube and a single venting tube, the venting tube being held in a fixed position relative to the inlet port. The apparatus includes a container 31, with a threaded neck 40 with which there is a screw-engaged cap 41. A sealing ring 42, forms an airtight seal between the container 31 and the cap 41. The cap 41 incorporates an inlet port 32 and a gas exit passage 34 leading to a capillary tube 37 located in the exit passage by a neoprene sealing cone 36. A venting tube 38 is held in position over the capillary tube 37 by a collar 35. The collar 35, which is located by a recess 44 in the cap 41, frictionally holds the venting tube 38 so that the venting tube can be adjustably moved in the vertical direction. The venting tube 38 opens only at the lower end in a mouth 45. The collar 35, is provided with an exit hole 46 and the cap 41 is provided with an intake hold 47. The cap 41 is also provided with a gas intake 48 that communicates with a flexible tube 49 connected to a fine-bore capillary tube 50. The fine-bore capillary tube 50 is connected to a length of flexible tube 52 which communicates with gas under pressure 62 through an on-off valve 51. To hold the device in a fixed position, the cap 41 is firmly attached to a rigid supporting piece 53.

In operation, gas 62 under pressure is allowed in to the container 31 through the capillary tube 50 by controlling the valve 51. The device is then immersed in a liquid and held in a fixed position by support 53 so that the liquid surface 54 is higher than the opening 45. Liquid flows into the container 31 through the inlet hold 32 forming a meniscus 33 at the internal end of the hole. The diameter of the inlet hole 32 is such that the surface tension of the liquid at the meniscus is sufficient to prevent gas from leaving the container 31 through the inlet hole 32. As liquid flows through the inlet hole 32, the meniscus 33 forms drops of liquid, which fall to the bottom of the container 31 to form a free surface of liquid 54b. Inlet hole 32 provides negligible resistance to the inflowing liquid and therefore the gas pressure within the container 31 is equal to the head represented by the distance H1. Liquid flows through the intake hole 47 into the space 55 between the collar 35 and the cap 41 to form a liquid surface 54c at the opening 45. The gas pressure within the venting tube 38 is equal to the hydraulic head represented by the distance H2. The pressure difference across capillary tube 37 is therefore equal to the head of liquid represented by the distance H. The distance H is a constant value and therefore gas must leave the enclosed chamber at constant rate determined only by the distance H and the frictional flow coefficient K of the capillary tube. This indirectly controls the rate at which liquid can enter the container 31. Thus by adjusting the position of the venting tube 38, the distance H can be varied and hence the pressure difference across the capillary tube 37 can be pre-set. By selecting a capillary tube 37, with an appropriate frictional flow coefficient K, this device can be used to obtain a sample of liquid representing the time-averaged state of that liquid while the device was immersed in the liquid.

Figure 2:
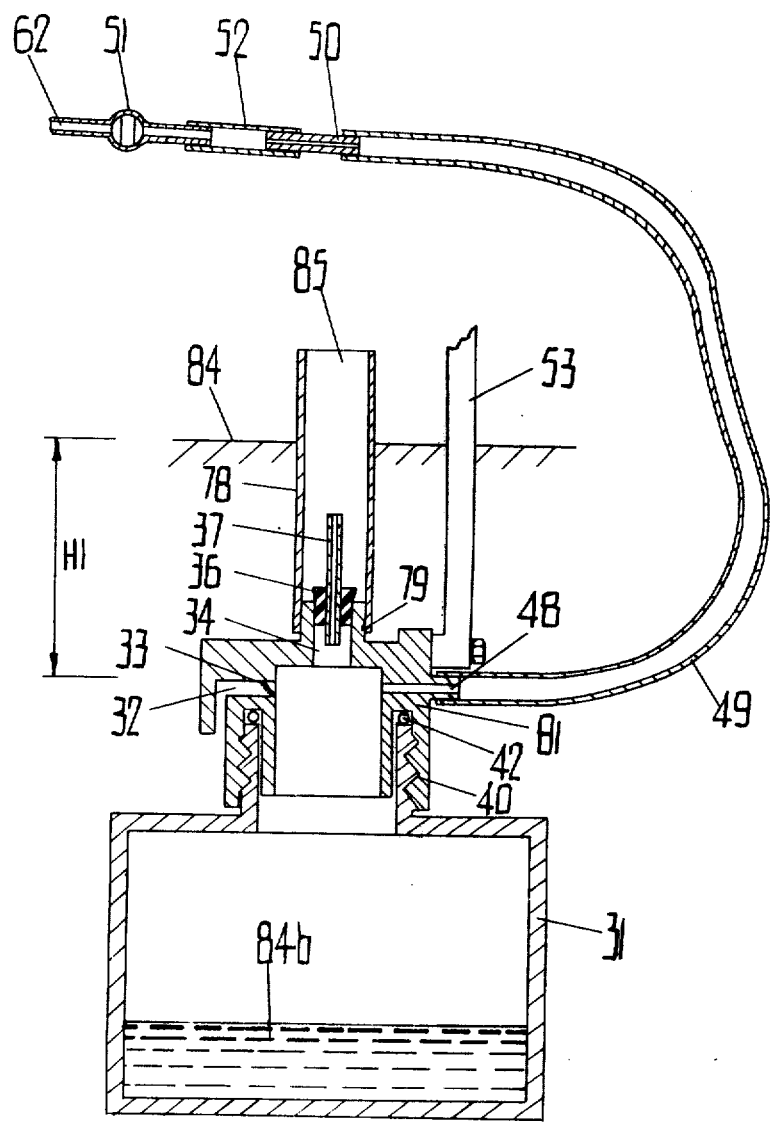
FIG. 2 is a diagrammatic sectional view of a second embodiment of the invention.

Referring to FIG. 2, the apparatus shown is similar to that described with respect to FIG. 1, and similar parts carry identical reference numerals.

In this embodiment the venting tube 78 is open at both ends, so that air passing through the capillary tube 37 leaves by a mouth 85 at the top of the venting tube 78. In this embodiment, therefore, the liquid intake 47 and the air exit hole 46 are both omitted. Further, the venting tube may be fixed relative to the cap 81.

The pressure difference across the capillary tube is equal to the head of liquid represented by the distance H1. Thus the flow of gas through the capillary tube 37 is related to the vertical position of the inlet hole 32 below the surface of the liquid 84 and to the frictional flow coefficient K of the capillary tube 37. This indirectly controls the rate at which liquid can enter the container 31.

Figure 3:
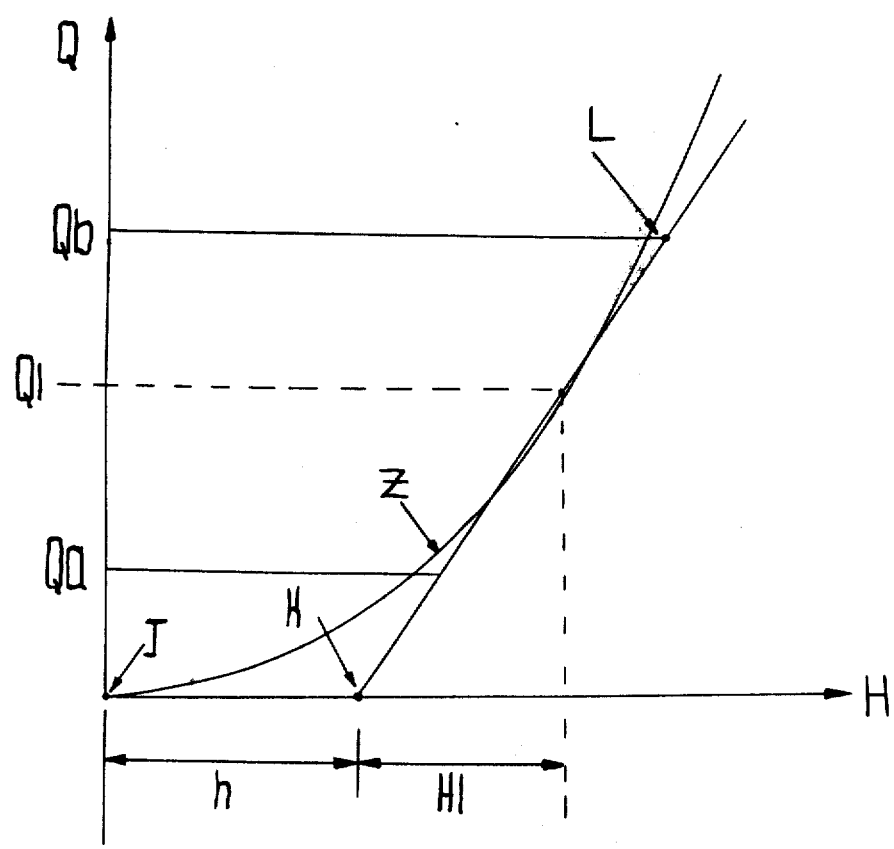
FIG. 3 is a graph showing a relationship between flow rate through the apparatus of FIG. 5 and depth of liquid.

One application for this device is in taking samples from a liquid passing through a channel where there is a known relationship Z between the depth H of liquid in the channel and the volume rate at which liquid is passing along that channel. According to FIG. 3 such a relationship is represented approximately by two straight lines J to K and K to L that define a relationship between the volume rate Q1 at which gas leaves the container 31 and the depth H1 of immersion of the inlet hole 32. In this situation, the sampling rate is approximately proportional to the rate of flow of liquid through a channel only when the flow rate is between prescribed limits; that is between $Q = Qa$ and $Q = Qb$. Outside this range, the sampling rate will not be representative of the flow rate through the channel. To obtain the straight line relationship J to K and K to L shown on FIG. 3.

a. the inlet hole 32 must be located a distance $h$ vertically above the zero flow level in the channel and b. the flow coefficient for capillary tube 37 must be chosen such that $$K = \frac{Q}{H - h}$$

The flow coefficient $K$ should also be chosen so that the volume rate of flow of gas from the container 31 should nearly empty the container of gas in the period of time during which the device is required to take samples.

The above description of the preferred embodiments of the invention is exemplary, and modifications to and variations of the specific embodiments could be made within the true scope of the invention, which is to be defined by the appended claims.

I claim:

1. Apparatus for sampling a liquid comprising:

a container for immersion in the liquid to a selected depth, the container including a closure means having a liquid intake means comprised of an elongated horizontal bore opening into the upper portion of the container through said closure means, said bore having a diameter at the point where it opens into said container of a size whereby a meniscus is formed by the surface tension of the liquid thereby preventing gas from exiting the container through said liquid inlet means when said meniscus is formed;

a gas exit passage means for selectively providing restricted flow of gas from the top of said container; and an elongated adjustable venting tube surrounding a vertical capillary tube in the closure means in communication with said bore opening for controlling the liquid flow rate into the container.

* * * * *